United States Patent [19]

Berk et al.

[11] Patent Number: 5,389,598

[45] Date of Patent: Feb. 14, 1995

[54] AQUEOUS CONCENTRATE FORMULATIONS HAVING REDUCED EYE IRRITANCY

[75] Inventors: Howard C. Berk, St. Louis County, Mo.; James W. Kassebaum, Indianapolis, Ind.

[73] Assignee: Monsanto Company, St. Louis, Mo.

[21] Appl. No.: 169,693

[22] Filed: Dec. 17, 1993

[51] Int. Cl.6 .............. A01N 57/04; A01N 28/30; A01N 25/32
[52] U.S. Cl. .................. 504/206; 504/116; 71/DIG. 1
[58] Field of Search .............. 504/206, 116; 71/DIG. 1

[56] References Cited

U.S. PATENT DOCUMENTS

| | | | |
|---|---|---|---|
| 5,118,444 | 6/1992 | Nguyen | 252/390 |
| 5,206,021 | 4/1993 | Dookhith et al. | 424/405 |
| 5,284,819 | 2/1994 | Zorner et al. | 504/127 |

*Primary Examiner*—Richard L. Raymond
*Assistant Examiner*—S. Mark Clardy
*Attorney, Agent, or Firm*—Stanley M. Tarter; Gordon F. Sieckmann; Richard H. Shear

[57] ABSTRACT

Disclosed are storage-stable aqueous concentrate formulations of pesticides or plant growth modifying agents containing sufficient amounts of an alkoxylated alkylamine surfactant to insure a high degree of pesticidal or plant growth modifying efficacy, wherein irritancy to eyes resulting from the presence of said surfactant is reduced by the presence of an effective amount of a $C_{6-22}$ saturated or unsaturated alkyl monocarboxylic or dicarboxylic acid or mixture of such acids.

20 Claims, No Drawings

AQUEOUS CONCENTRATE FORMULATIONS HAVING REDUCED EYE IRRITANCY

FIELD OF THE INVENTION

This invention comprises new and useful storage-stable aqueous concentrate compositions of pesticides or plant growth modifying agents, in particular the herbicide N-phosphonomethylglycine or its salts or mixtures thereof, containing sufficient amounts of an alkoxylated alkylamine surfactant to insure a high degree of pesticidal or plant growth modifying efficacy, wherein irritancy to eyes resulting from the presence of said surfactant is significantly reduced or eliminated by the presence in the formulation of a small quantity of a $C_{6-22}$ saturated or unsaturated alkyl monocarboxylic or dicarboxylic acid or mixture of such acids.

BACKGROUND OF THE INVENTION

Aqueous concentrate formulations of pesticidal and plant growth modifying chemicals are widely used in agricultural, industrial, recreational and residential areas worldwide. The chemicals which form the active ingredients of such formulations illustratively include insecticides, fungicides, herbicides, plant growth regulators and plant nutrients. An aqueous concentrate is essentially a solution of the active ingredient in water at relatively high concentration, intended for dilution in water prior to application by spraying or other means. Typically the aqueous concentrate is diluted in about 10 to about 100 times its own volume of water prior to application.

If the active ingredient is to be applied to the foliage of plants, a surfactant is typically included in the formulation to aid wetting of the foliage by the spray solution and improve retention and uptake of the active ingredient by the plant. Because the spray solution must contain a sufficient concentration of said surfactant to provide good wetting, retention and uptake, and therefore good efficacy, the aqueous concentrate formulation must generally contain a high concentration of the surfactant, typically about 5% to about 25% by weight of the formulation.

A common concern with many surfactants that provide good efficacy of the active ingredient is that at the high concentrations required in the aqueous concentrate formulation the surfactants tend to be irritant if accidentally splashed or otherwise injected into the eye of anyone handling such a formulation. This property may lead to restrictive labelling of the product that limits its usefulness in certain markets, even where the active ingredient itself provides no such hazard.

A class of surfactants that are known to give excellent efficacy of certain foliar-applied pesticides and plant growth modifying agents, but are irritant to eyes at the high concentrations required in aqueous concentrate formulations, are alkoxylated alkylamines. These are especially widely used in aqueous concentrate formulations of the herbicide N-phosphonomethylglycine, commonly known as glyphosate.

Glyphosate is a highly effective and commercially important herbicide useful for combating the presence of a wide variety of unwanted vegetation, including agricultural weeds. Glyphosate is applied as a formulated product to the foliage of annual and perennial grasses, sedges and broadleaf plants and the like, and is taken up over a period of time through the leaves into the treated vegetation, whence it translocates throughout the plant.

Glyphosate in its acid form has relatively low water solubility, but when formulated as a salt its solubility is much higher. Aqueous concentrate formulations of glyphosate therefore typically contain one or more salts, such as an alkylamine, for example, isopropylammonium, salt, the ammonium salt, the trimethylsulfonium salt or an alkali metal, for example potassium or sodium, salt of glyphosate.

A wide variety of alkoxylated alkylamine surfactants have been tested or used commercially in glyphosate formulations. They may be represented generically by the structural formula

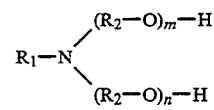

wherein $R_1$ is $C_{8-22}$ alkyl, $R_2$ groups are $C_{2-4}$ alkylene groups or a mixture of such groups and m and n are numbers such that m+n has an average value in the range from about 2 to about 50. In commercial formulations $R_1$ is most commonly derived from a natural source such as tallow, soybean or coconut oil and comprises a range of chain lengths, and $R_2$ is most commonly ethylene.

Aqueous concentrate formulations of the isopropylamine salt of glyphosate with a surfactant based on ethoxylated tallowamine have been sold by Monsanto Company for many years under various trade names including Roundup ® herbicide.

European patent application 0 290 416 discloses aqueous concentrate formulations of glyphosate or its salts with a surfactant having the structure represented above wherein $R_1$ is $C_{8-22}$ alkyl, $R_2$ is alkylene, for example ethylene or propylene, and m+n has an average value in the range from about 1 to about 12, and wherein the weight ratio of glyphosate (expressed as acid equivalent) to said surfactant is in the range from about 1:1.75 to about 6:1.

Eye irritant properties of alkoxylated alkylamine surfactants are well known, and are disclosed, for example, in Australian patent application 81718/91. This patent application discloses surfactant compositions comprising an alkoxylated alkylamine of the structure represented above wherein m+n has an average value of at least about 7, together with compounds said to reduce the eye irritancy of said alkoxylated alkylamine. The eye irritancy reducing agents disclosed include sulfated polyoxyalkylene alkylphenols, alcohol sulfates, polyoxyalkylene alcohol sulfates, mono- and dialcohol sulfates, mono- and di-(polyoxyalkylene alcohol) phosphates, mono- and di-(polyoxyalkylene alkylphenol) phosphates, polyoxyalkylene alkylphenol carboxylates and polyoxyalkylene carboxylates, said eye irritant reducing compounds having alkyl or alcohol groups with a chain length from about 8 to about 20 carbon atoms and up to about 60 moles of alkylene oxide per mole of the compound. It is further disclosed that said surfactant compositions can be used to prepare pesticidal compositions, particularly herbicidal compositions containing glyphosate.

There are provided herein new and useful storage-stable aqueous concentrate compositions comprising (a) a water-soluble pesticide or plant growth modifying agent, (b) an alkoxylated alkylamine surfactant having the molecular structure represented above in sufficient amount to provide good efficacy of said pesticide or plant growth modifying agent when the composition is applied in diluted form to plant foliage, (c) a $C_{6-22}$ saturated or unsaturated alkyl monocarboxylic or dicarboxylic acid or mixture of such acids and (d) water; said compositions being less irritant to eyes than similar compositions lacking only component (c).

Saturated or unsaturated alkyl monocarboxylic or dicarboxylic acids have not previously been disclosed to act as eye irritancy reducing agents when used with eye irritant surfactants, such as alkoxylated alkylamines. They have advantages over the eye irritation reducing agents disclosed in Australian patent application 81718/91 cited above in having lower cost.

U.S. Pat. No. 5,196,044 discloses that fatty acids of carbon chain length from about 7 to about 20 may be used in combination with certain herbicides, including glyphosate based herbicides, to give improved herbicidal performance. Examples are provided wherein nonanoic acid, in the form of an 80% (by weight) formulation called Sharpshooter ® herbicide, was diluted as a spray mix together with the isopropylamine salt of glyphosate, in the form of Roundup ® herbicide. No disclosure is made of an aqueous concentrate formulation comprising a herbicidal active ingredient, an alkoxylated alkylamine surfactant and a saturated or unsaturated fatty acid. No mention is made of eye irritancy properties of any composition disclosed; nor is any guidance given as to how to prepare a storage-stable aqueous concentrate formulation comprising both glyphosate and saturated or unsaturated fatty acid. The spray mixes disclosed contain a sufficient quantity of the fatty acid to provide enhanced weed control performance by comparison with the herbicide alone. For example, the weight/weight ratios of nonanoic acid to glyphosate (expressed as acid equivalent) in disclosed spray mixes ranged from 1:3 to 62:1.

PCT application WO 92/07467 discloses dilute aqueous compositions comprising glyphosate or derivatives or salts thereof together with a fatty acid or fatty acid salt, which are said to provide herbicidal activity at rates lower than those of either component alone required to provide comparable activity. The fatty acid or fatty acid salt component is present in the range from 0.1% to 3.0% by weight of the composition while the glyphosate component is present at 0.08% to 2.0% by weight of the composition. Again, no mention is made of eye irritancy properties of any composition disclosed; nor is any guidance given as to how to prepare a storage-stable aqueous concentrate formulation comprising both glyphosate and fatty acid. All data provided relate to dilute mixtures of Roundup ® herbicide with fatty acid salts as opposed to fatty acids, with the exception of data provided in Table 4 of the cited application. This Table 4 presents data on various dilute mixtures of Roundup herbicide with a 1:1 formulation of soybean and coconut fatty acids. These mixtures, when compared with Roundup herbicide alone, are shown to provide slightly superior herbicidal efficacy on two weed species and inferior herbicidal efficacy on a third weed species.

European patent application 0 566 648 discloses aqueous formulations comprising a salt of glyphosate and at least one fatty acid or salt thereof, wherein the fatty acid or salt thereof is present in an amount sufficient to provide herbicidal activity in its own right, in the form of early contact injury symptoms. An appropriate pH range is disclosed (about 6.4 to about 7.8, preferably about 6.8 to about 7.0) wherein said formulations are said to show improved storage stability while maintaining the desired herbicidal efficacy. Among surfactants disclosed as optional components of said formulations is an ethoxylated tallowamine surfactant having about 15 to about 18 moles of ethylene oxide per mole of tallowamine. Once again, no mention is made of eye irritancy properties of any composition disclosed. No hint is present that any advantage might be apparent at fatty acid concentrations far below those providing contact injury symptoms, or at pH levels more typical of commercial aqueous concentrate formulations of glyphosate, such as in the range from about 4.0 to about 6.0.

SUMMARY OF THE INVENTION

This invention comprises new and useful storage-stable aqueous concentrate compositions of pesticides or plant growth modifying agents, in particular the herbicide N-phosphonomethylglycine (glyphosate) or its salts or mixtures thereof, having unexpectedly low irritancy to eyes. Compositions of the invention contain, in addition to one or more active ingredients and water, an alkoxylated alkylamine surfactant represented generically by the structural formula

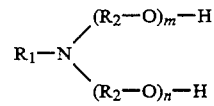

wherein $R_1$ is $C_{18-22}$ alkyl, $R_2$ groups are $C_{2-4}$ alkylene groups or a mixture of such groups and m and n are numbers such that m+n has an average value in the range from about 2 to about 50, said alkoxylated alkylamine surfactant being present in sufficient amount to insure a high degree of pesticidal or plant growth modifying efficacy. At such levels in a concentrate formulation, an alkoxylated alkylamine surfactant of chemical structure represented above normally imparts to the formulation an undesirable degree of irritancy to eyes. In compositions of the invention, irritancy to eyes resulting from the presence of said alkoxylated alkylamine surfactant is significantly reduced or eliminated by the presence in the formulation of a $C_{6-22}$ alkyl monocarboxylic or dicarboxylic acid or mixture of such acids. Surprisingly, the amount of said monocarboxylic or dicarboxylic acid(s) required in the formulation to provide useful eye irritancy reduction is much lower than amounts of fatty acids previously disclosed to give other benefits, such as herbicidal performance enhancement. Compositions of the present invention comprise alkoxylated alkylamine surfactant and monocarboxylic or diacrboxylic acid(s) in a weight/weight ratio ranging from about 2:1 to about 20:1. Glyphosate formulations of the invention comprise glyphosate (on an acid equivalent basis) and monocarboxylic or dicarboxylic acid(s) in a weight/weight ratio ranging from about 5:1 to about 100:1. No adverse effect on pesticidal or plant growth modifying performance is produced by inclusion of monocarboxylic or dicarboxylic acid(s) at such levels in formulations of the invention. Glyphosate formulations of the invention have commercially acceptable storage stability at pH levels typical of aqueous concentrate formulations of glyphosate, such as in the range from about 4.0 to about 6.0.

OBJECTS OF THE INVENTION

It is an object of the present invention to provide an aqueous concentrate formulation of a pesticidal or plant growth modifying active ingredient which combines a high degree of efficacy for its intended purpose with low eye irritancy.

It is a further object of the present invention to provide such an aqueous concentrate formulation having commercially acceptable storage stability.

It is a still further object of the present invention to provide such an aqueous concentrate formulation at relatively low cost by comparison with previously disclosed solutions to the eye irritancy problem.

It is a particular object of the invention to provide aqueous concentrate formulations meeting the criteria set forth in the immediately preceding three paragraphs, wherein the active ingredient is the herbicide glyphosate and the surfactant system present in the formulation comprises an alkoxylated alkylamine surfactant of a type normally imparting an undesirable degree of eye irritancy to the formulation.

These and other objects are satisfied in compositions of the invention described in detail below.

DETAILED DESCRIPTION OF THE INVENTION

There are provided herein compositions comprising:

(a) a water-soluble pesticide or plant growth modifying agent, in an amount sufficient to provide the desired pesticidal or plant growth modifying effect when the composition is diluted by a factor of at least 10 in water and applied to the organism to be killed, controlled or modified;

(b) an alkoxylated alkylamine surfactant represented generically by the structural formula

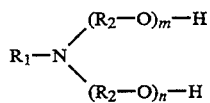

wherein $R_1$ is a straight or branched chain alkyl group with an average of about 8 to about 22 carbon atoms, $R_2$ groups are $C_{2-4}$ alkylene groups or a mixture of such groups and m and n are numbers such that m+n has an average value in the range from about 2 to about 50, said alkoxylated alkylamine surfactant being present in sufficient amount to provide good efficacy of said pesticide or plant growth modifying agent when the composition is applied in diluted form to the organism to be killed, controlled or modified, and in sufficient amount to impart an undesirable degree of eye irritancy to the composition if component (c) is absent;

(c) a $C_{6-22}$ saturated or unsaturated alkyl monocarboxylic or dicarboxylic acid or mixture of such acids, in sufficient amount to reduce or eliminate the eye irritancy of the composition imparted by component (b), but in an amount insufficient to cause any herbicidal symptoms in its own right when the composition is applied in diluted form to plant foliage; and (d) water.

Active ingredients useful in compositions of the invention may be fungicides, insecticides, acaricides, miticides, herbicides, plant growth regulators, plant nutrients or other pesticidal or plant growth modifying agents. The only limitation is that they have sufficient solubility in water to be formulatable as aqueous concentrates at about 10 times the concentration required in an application solution.

Especially useful active ingredients in compositions of the present invention are water-soluble herbicides, including but not restricted to salts of phenoxyacetic, phenoxypropionic and phenoxybutyric acids, salts of dicamba, salts of picloram, salts of dalapon, salts of acifluorfen, salts of glyphosate, salts of glufosinate, salts of methanearsonic acid, mixtures thereof and the like. Preferred among these are salts of glyphosate, more especially alkali metal, ammonium, alkylammonium and trimethylsulfonium salts. Compositions of the invention are useful whether single salts of glyphosate, such as the isopropylamine salt, mixtures of salts of glyphosate, or mixtures comprising glyphosate salt(s) and at least one other water-soluble herbicide, are to be formulated.

In glyphosate salt formulations of the invention, glyphosate (expressed as acid equivalent) is typically present at about 10% to about 40% by weight, preferably at about 25% to about 35% by weight, of the formulation.

In the structure of the alkoxylated alkylamine surfactant present in compositions of the invention, $R_1$ is preferably a straight chain alkyl group with an average of about 12 to about 18 carbon atoms. The alkyl chain may be derived naturally or synthetically. Typically it is derived from a natural source such as coconut or soybean oil or tallow. Preferred alkylamines include dodecylamine, stearylamine, cocoamine and tallowamine.

$R_2$ in the structure of said alkoxylated alkylamine surfactant is preferably ethylene, and m+n preferably has an average value from about 2 to about 20.

Glyphosate formulations of the invention typically contain glyphosate salt (expressed as acid equivalent) and alkoxylated alkylamine surfactant in a weight/weight ratio ranging from about 10:1 to about 1:2, preferably from about 5:1 to about 2:1.

Acids useful as eye irritancy reducing agents in formulations of the invention include monocarboxylic acids, such as octanoic, nonanoic, decanoic, dodecanoic and octodecanoic acids, and dicarboxylic acids, such as adipic acid. A mixture of such acids may be used, and will be normal where these are derived from a natural source, such as coconut oil. An especially preferred acid is octanoic acid.

To obtain the desired reduction in eye irritancy, the weight/weight ratio of alkoxylated alkylamine surfactant to $C_{8-22}$ alkyl monocarboxylic or dicarboxylic acid(s) in formulations of the invention is in the range from about 2:1 to about 20:1.

Glyphosate formulations of the invention comprise glyphosate (on an acid equivalent basis) and monocarboxylic or dicarboxylic acid(s) in a weight/weight ratio ranging from about 10:1 to about 100:1, preferably from about 10:1 to about 40:1. An example with a glyphosate/octanoic acid ratio of about 8:1 was found not to give useful improvement in eye irritancy. It appears that it is possible to have too much, as well as too little, of the monocarboxylic or dicarboxylic acid to give the desired effect. In addition, at very low glyphosate/fatty acid ratios, there may be sufficient fatty acid present to have a direct phytotoxic effect, with the attendant danger of antagonizing the long-term herbicidal efficacy of the glyphosate component.

Optionally, ingredients other than those specified in (a) to (d) above may be present in aqueous concentrate formulations of the invention. These include, but are not limited to, dyes, thickeners, stabilizers, cosurfactants, gel inhibitors, antifreezes, anti-foam agents, mixtures thereof and the like. Where the alkoxylated alkylamine surfactant is one that tends to form a gel on adding to water, a particularly useful added ingredient is a glycol, for example a polyethylene glycol having an average molecular weight in the range from about 300 to about 1000, which acts as a gel inhibitor.

Compositions of the invention show good storage stability across a wide range of temperatures. They do not show crystallization of active or other ingredients at low temperatures, for example around 0° C., nor do they show phase separation at high temperatures, for example around 50° C. The tendency for phase separation can be measured by cloud point, which is the temperature at which phase separation begins. For commercial acceptability in most markets, cloud point must normally be around 50° C. or higher.

In the case of glyphosate formulations of the invention, good storage stability has been observed at pH levels far below those required for more dilute formulations with a much lower glyphosate/fatty acid ratio, as disclosed in EP application 566,648 cited above. Typically the pH of glyphosate formulations of the invention is in the range from about 4.0 to about 6.0, but pH levels outside this range may also be acceptable.

The present invention is illustrated by but not limited to the following working examples. In describing concentrate compositions of the examples, percentages are given by weight unless otherwise indicated.

EXAMPLES

In the following Examples, eye irritancy was determined by testing in full accordance with United States EPA Publication 540/9-84-014, November 1984: Pesticidal Assessment Guidelines, Subdivision F, Hazard Evaluation (Human and Domestic Animals). Studies were conducted in compliance with EPA Good Laboratory Practice Standards as set out in Federal Register, Vol. 48, Nov. 29, 1983. Test materials were classified into toxicity categories as follows:

| Category | Criteria |
| --- | --- |
| I | Corrosive (irreversible destruction of ocular tissue) or corneal involvement or conjunctival irritation persisting through day 21. |
| II | Corneal involvement or conjunctival irritation clearing in 8-21 days. |
| III | Corneal involvement or conjunctival irritation clearing in 7 days or less. |
| IV | Minimal effects clearing in less than 24 hours. |

The practice of the present invention provides reduced irritation as reflected by at least one higher eye irritancy category as determined by the just-mentioned EPA publication.

Example 1 (representative of prior art)

An aqueous solution of the isopropylamine salt of glyphosate, containing 61.3% of said salt, was used as the starting material for preparing an aqueous concentrate of prior art. To 68.5 g of this solution was added (1) 7.2 g of an ethoxylated tallowamine surfactant containing an average of about 15 moles of ethylene oxide per mole of tallowamine, (2) 2.8 g of polyethylene glycol with an average molecular weight of about 600, and having small amounts of monoethylene glycol and water as impurities, and (3) 21.5 g of water, with stirring to make 100 g of an aqueous concentrate formulation.

The formulation of Example 1 was tested for eye irritancy as described above. On the basis of results from this testing, it was placed in toxicity category I. This formulation has a pH of 4.7 when diluted at the rate of 5 g in 100 ml water. Its cloud point is 81° C.

Example 2 (representative of the present invention)

An aqueous solution of the isopropylamine salt of glyphosate, containing 61.3% of said salt, was used as the starting material for preparing an aqueous concentrate of prior art. To 68.5 g of this solution was added (1) 7.2 g of an ethoxylated tallowamine surfactant containing an average of about 15 moles of ethylene oxide per mole of tallowamine, (2) 2.0 g of polyethylene glycol with an average molecular weight of about 400, (3) 0.8 g of octanoic acid, and (4) 21.5 g of water, with stirring to make 100 g of an aqueous concentrate formulation.

The formulation of Example 2 was tested for eye irritancy as described above. On the basis of results from this testing, it was placed in toxicity category III. By comparison with the formulation of Example 1, which is of very similar composition but lacking octanoic acid, eye irritancy is therefore very significantly reduced. The formulation of Example 2 has a pH of 4.7 when diluted at the rate of 5 g in 100 ml water. Its cloud point is 64° C.

Extensive greenhouse and field evaluation of the herbicidal efficacy of the formulation of Example 2 was conducted. Its performance has been found to be very similar to that of commercial standards containing similar or higher levels of tallowamine 15-mole ethoxylate surfactant but no octanoic acid.

Example 3 (representative of prior art)

An aqueous solution of the isopropylamine salt of glyphosate, containing 61.3% of said salt, was used as the starting material for preparing an aqueous concentrate of prior art. To 68.5 g of this solution was added (1) 10.0 g of an ethoxylated cocoamine surfactant containing an average of about 2 moles of ethylene oxide per mole of cocoamine, and (2) 21.5 g of water, with stirring to make 100 g of an aqueous concentrate formulation.

The formulation of Example 3 was tested for eye irritancy as described above. On the basis of results from this testing, it was placed in toxicity category I. This formulation has a pH of 5.1 when diluted at the rate of 5 g in 100 ml water. Its cloud point is higher than 95° C.

Example 4 (representative of the present invention)

An aqueous solution of the isopropylamine salt of glyphosate, containing 61.3% of said salt, was used as the starting material for preparing an aqueous concentrate of prior art. To 68.5 g of this solution was added (1) 10.0 g of an ethoxylated cocoamine surfactant containing an average of about 2 moles of ethylene oxide per mole of cocoamine, (2) 2.0 g of octanoic acid, and (3) 19.5 g of water, with stirring to make 100 g of an aqueous concentrate formulation.

The formulation of Example 4 was tested for eye irritancy as described above. On the basis of results from this testing, it was placed in toxicity category II. By comparison with the formulation of Example 3, which is of very similar composition but lacking octanoic acid, eye irritancy is therefore significantly reduced. This formulation has a pH of 5.0 when diluted at the rate of 5 g in 100 ml water. Its cloud point was determined to be higher than 95° C.

Greenhouse evaluation of the herbicidal efficacy of the formulation of Example 4 was conducted. Its performance has been found to be very similar to that of commercial standards containing tallowamine 15-mole ethoxylate surfactant but no octanoic acid.

While the illustrative embodiments of the invention have been described with particularity, it will be understood that various other modifications will be apparent to and can readily be made by one of skill in the art without departing from the spirit and scope of the invention.

What is claimed is:

1. A storage-stable aqueous concentrate composition comprising
   (a) a water-soluble pesticide or plant growth modifying agent, in an amount sufficient to provide the desired pesticidal or plant growth modifying effect when the composition is diluted by a factor of at least 10 in water and applied to the organism to be killed, controlled or modified;
   (b) an alkoxylated alkylamine surfactant represented generically by the structural formula

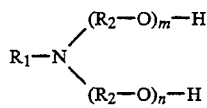

wherein $R_1$ is a straight or branched chain alkyl group with an average of about 8 to about 22 carbon atoms, $R_2$ groups are $C_{2-4}$ alkylene groups or a mixture of such groups and m and n are numbers such that m+n has an average value in the range from about 2 to about 50, said alkoxylated alkylamine surfactant being present in sufficient amount to provide good efficacy of said pesticide or plant growth modifying agent when the composition is applied in diluted form to the organism to be killed, controlled or modified, and in sufficient amount to impart an undesirable degree of eye irritancy to the composition if component (c) is absent;
   (c) a $C_{6-22}$ saturated or unsaturated alkyl monocarboxylic or dicarboxylic acid or mixture of such acids, in sufficient amount to reduce or eliminate the eye irritancy of the composition imparted by component (b), but in an amount insufficient to cause any herbicidal symptoms in its own right when the composition is applied in diluted form to plant foliage in accordance with the present invention; and
   (d) water.

2. The composition of claim 1 wherein component (a) is a salt, or mixture of salts, of glyphosate.

3. The composition of claim 2 wherein component (a) is an alkali metal, ammonium, alkylammonium or trimethylsulfonium salt of glyphosate, or a mixture of said salts.

4. The composition of claim 3 wherein component (a) is the isopropylamine salt of glyphosate.

5. The composition of claim 2 wherein $R_1$ in the structure of component (b) is a straight chain alkyl group with an average of about 12 to about 18 carbon atoms.

6. The composition of claim 2 wherein component (b) is an alkoxylated dodecylamine, stearylamine, cocoamine or tallowamine.

7. The composition of claim 2 wherein $R_2$ in the structure of component (b) is ethylene.

8. The composition of claim 6 wherein $R_2$ in the structure of component (b) is ethylene and m+n in the structure of component (b) has an average value in the range from about 2 to about 20.

9. The composition of claim 8 wherein glyphosate (expressed as acid equivalent) and ethoxylated alkylamine surfactant are present in a weight/weight ratio ranging from about 10:1 to about 1:2.

10. The composition of claim 8 wherein glyphosate (expressed as acid equivalent) and ethoxylated alkylamine surfactant are present in a weight/weight ratio ranging from about 5:1 to about 2:1.

11. The composition of claim 2 wherein component (c) is a saturated or unsaturated alkyl monocarboxylic acid with an alkyl chain length of about 8 to about 18 carbon atoms.

12. The composition of claim 8 wherein component (c) is octanoic acid.

13. The composition of claim 8 wherein components (b) and (c) are present in a weight/weight ratio in the range from about 2:1 to about 20:1.

14. The composition of claim 8 wherein glyphosate (expressed as acid equivalent) and component (c) are present in a weight/weight ratio ranging from about 10:1 to about 100:1.

15. The composition of claim 8 wherein glyphosate (expressed as acid equivalent) and component (c) are present in a weight/weight ratio ranging from about 10:1 to about 40:1.

16. The composition of claim 8 having a pH in the range from about 4.0 to about 6.0.

17. A storage-stable aqueous concentrate composition comprising
   (a) a water-soluble salt of glyphosate in a concentration such that when the composition is diluted by a factor of at least 10 with water and applied to vegetation the glyphosate is present in an amount sufficient to control such vegetation;
   (b) an ethoxylated (EO=2−20) $C_{8-22}$ alkylamine surfactant in an amount sufficient to enhance the herbicidal efficacy of glyphosate when applied in diluted form but in a sufficient amount to impart an undesirable degree of eye irritancy to the composition before dilution when component (c) is absent from the composition;
   (c) a $C_{6-22}$ saturated alkyl monocarboxylic acid in an amount to reduce the eye irritancy of the composition imparted by the presence of component (b) as indicated by at least one higher eye irritancy category as determined in accordance with United States EPA publication 540/9-84-014, November 1984: Pesticidal Assessment Guidelines, Subdivision F, Hazard Evaluation (Human and Domestic Guidelines); and
   (d) water.

18. The composition of claim 17 wherein component (a) is an alkali metal, alkylammonium or trimethyl-sulfonium salt of glyphosate, or a mixture of such salts.

19. The composition of claim 18 wherein component (b) is ethoxylated tallowamine.

20. The composition of claim 19 wherein component (c) is octanoic acid.

* * * * *